(12) United States Patent
Bühlmann

(10) Patent No.: US 11,848,587 B2
(45) Date of Patent: Dec. 19, 2023

(54) SURGICAL MICROMOTOR

(71) Applicant: BIEN-AIR HOLDING SA, Biel/Bienne (CH)

(72) Inventor: David Bühlmann, La Chaux-de-Fonds (CH)

(73) Assignee: Bien-Air Holding SA c/o Bien-Air Dental SA, Biel/Bienne (CH)

( * ) Notice: Subject to any disclaimer, the term of this patent is extended or adjusted under 35 U.S.C. 154(b) by 0 days.

(21) Appl. No.: 18/013,004

(22) PCT Filed: Jul. 7, 2021

(86) PCT No.: PCT/EP2021/068894
§ 371 (c)(1),
(2) Date: Dec. 27, 2022

(87) PCT Pub. No.: WO2022/008618
PCT Pub. Date: Jan. 13, 2022

(65) Prior Publication Data
US 2023/0190324 A1    Jun. 22, 2023

(30) Foreign Application Priority Data
Jul. 7, 2020 (EP) .................................. 20184558

(51) Int. Cl.
*H02K 1/2783* (2022.01)
*H02K 1/02* (2006.01)
(Continued)

(52) U.S. Cl.
CPC ............. *H02K 1/2783* (2022.01); *H02K 1/02* (2013.01); *H02K 7/003* (2013.01);
(Continued)

(58) Field of Classification Search
CPC ........ H02K 1/2783; H02K 1/02; H02K 7/003; H02K 1/2733; H02K 21/14; H02K 21/16;
(Continued)

(56) References Cited

U.S. PATENT DOCUMENTS 8,596,999 B2   12/2013   Tadahiko et al.
10,033,250 B2   7/2018   Tremelling et al.
(Continued)

FOREIGN PATENT DOCUMENTS

| CA | 3073178 A1 | 2/2019 |
| WO | 2010135992 A1 | 12/2010 |
| WO | 2018068369 A1 | 4/2018 |

OTHER PUBLICATIONS

International Search Report issued in corresponding application No. PCT/EP2021/068894 dated Oct. 15, 2021, 6 pages.
(Continued)

*Primary Examiner* — Shawki S Ismail
*Assistant Examiner* — Htet Z Kyaw
(74) *Attorney, Agent, or Firm* — Pearne & Gordon LLP

(57) ABSTRACT

The present invention relates to a rotary micromotor (10) designed for actuating an abrasive blade (4) of a surgical or dental tool, the motor comprising a rotor (11) co-operating with a stator (12), and being characterized in that the rotor (11) has a hollow central tubular portion, and comprises an outwardly polarized Halbach array.

11 Claims, 4 Drawing Sheets

(51) Int. Cl.
*H02K 7/00* (2006.01)
*A61B 17/32* (2006.01)
*A61B 17/00* (2006.01)
*A61C 1/02* (2006.01)

(52) U.S. Cl.
CPC .................. *A61B 17/32002* (2013.01); *A61B 2017/00398* (2013.01); *A61B 2217/005* (2013.01); *A61C 1/02* (2013.01)

(58) Field of Classification Search
CPC .......... H02K 7/145; H02K 1/27; H02K 1/278; H02K 1/2792; H02K 1/28; H02K 7/14; H02K 1/32; H02K 9/00; A61B 17/32002; A61B 2017/00398; A61B 2217/005; A61B 2017/22079; A61C 1/02; A61C 1/06
USPC ...... 310/156.01, 61, 60 A, 50, 40 MM, 75 D
See application file for complete search history.

(56) References Cited

U.S. PATENT DOCUMENTS

| | | | |
|---|---|---|---|
| 2014/0111052 A1* | 4/2014 | Wu | H02K 21/14 |
| | | | 310/156.55 |
| 2015/0280523 A1* | 10/2015 | Tremelling | H02K 7/09 |
| | | | 29/598 |
| 2017/0126087 A1* | 5/2017 | Soderberg | H02K 1/2792 |
| 2020/0220439 A1* | 7/2020 | Sigmar | H02K 11/33 |
| 2021/0186524 A1* | 6/2021 | Carusillo | A61B 17/1637 |
| 2022/0381247 A1* | 12/2022 | Shirazee | F04D 13/064 |

OTHER PUBLICATIONS

Written Opinion issued in corresponding application No. PCT/EP2021/068894 dated Oct. 15, 2021, 11 pages.

\* cited by examiner

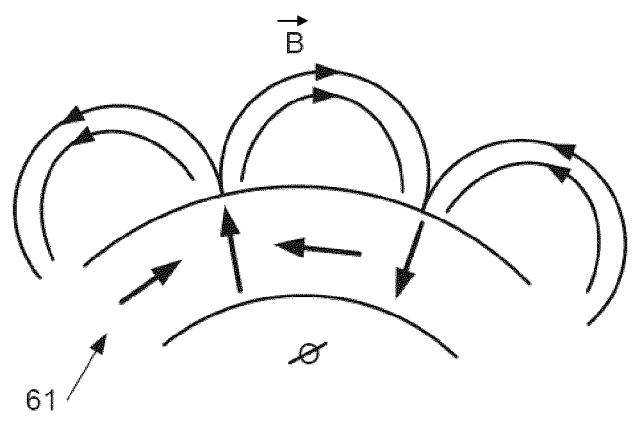 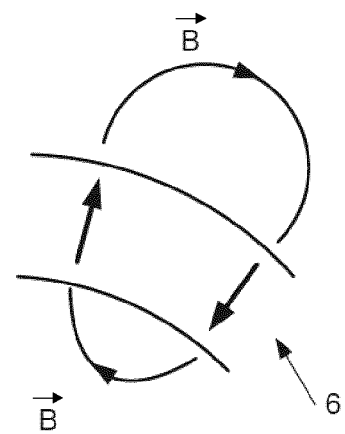
*Fig. 2A*  *Fig. 2B*

SURGICAL MICROMOTOR

TECHNICAL FIELD OF THE INVENTION

The present invention relates to the field of micromotors intended for dental or surgical applications. More specifically, it concerns a micromotor for a microdebrider provided with a cannulated shaft.

STATE OF THE ART

Surgical or dental motors with a conventional (rotor-stator) architecture are known, having generally a permanent magnet located in the rotor or in the stator of bipolar magnetization or radial multipolar magnetization. The presence of several magnetic poles makes it possible to obtain a more constant torque, but requires the presence of blocks or laminations of ferromagnetic material with low coercivity at the level of the rotor (of the mu-metal type, or preferably silicon iron or mild steel which saturate less quickly) in order to close the field lines between the poles, and thus not to lose in intensity of flux, this last one being correlated with the applied motor torque.

Nevertheless, for some surgical applications, it is preferable that a drive shaft be empty in the center so as to allow the suction of debris generated during the tissue removal operation along an integrated straight channel, in order to avoid having to build another dedicated evacuation channel, which requires additional space and complicates the cleaning operations, and to prevent such a channel from becoming blocked; this is the case, for example, for a microdebrider, which is usually referred to as a "shaver". In such a case, when the drive shaft is integral with the rotor and is not connected to the latter by a gear mechanism, it is necessary to provide a certain thickness made of magnetic material in order to achieve magnetic shielding with respect to the interior, in order not to disturb the flow of the liquid suction stream evacuating the debris resulting from the operation, which however results in a loss of volume available for the arrangement of the magnets.

Consequently, a drawback of the usual motors adapted to this type of tools is that the magnetic flux density is lower than those available for a solid shaft, which results in losses of power and therefore of performance. In addition, the configuration of the magnets or the plurality of magnets causes them to be in a state of magnetization that is not optimal, which increases the risk of demagnetization. Concerning more specifically the case of a multipolar rotor, the very precise configuration required makes its production particularly difficult and costly.

For larger parts, cylindrical arrangements based on Halbach arrays are also known, which are used in brushless motors, for example, to confine the magnetic flux to the center. These motors have better efficiencies and produce higher torques than a conventional magnetic arrangement, while achieving self-shielding with respect to the exterior. Nevertheless, such motors are difficult to miniaturize because, in order to avoid end effects and because of the difficulty of manufacturing a cylinder with a continuously varying field, they are generally designed in segments. Cylindrical Halbach arrays can also be used to make magnetic couplers, such as for example in one of the variants of a heart pump described in the patent document U.S. Pat. No. 8,596,999. However, this type of coupling solution implies a pair of nested coaxial cylinders with opposing magnetic fluxes, the significant bulk of which is hardly compatible with the operational constraints of micromotors. Another example of a machine that can use a Halbach array is provided in the American patent U.S. Pat. No. 10,033,250.

Micromotors for surgical handpieces with a central cannula to receive a drilling tool are also known, such as those described in the document CA 3,073,178.

Consequently there exists a need for a solution not having these known drawbacks.

SUMMARY OF INVENTION

One object of the present invention is to propose a solution making it possible to optimize the torque of a motor with a cannulated shaft (for example a microdebrider or shaver).

Another object of the present invention is to make possible the production of a multipolar rotor of more efficient construction, providing better transmission efficiency.

These objects are achieved according to the invention by means of a rotary micromotor designed to actuate an abrasive blade of a surgical or dental tool, comprising a rotor co-operating with a stator, the rotary motor being characterized in that the rotor has a hollow central tubular portion, and comprises an outwardly polarized Halbach array.

An advantage of the proposed solution is to maximize the volume available for magnets by dispensing with an internal shielding sheath of magnetic material.

Another advantage of the proposed solution, again thanks to the elimination of the shielding sheath which is generally made of a magnetic material such as mu-metal, and therefore relatively heavy, is to allow a reduction of the rotor inertia.

Still another advantage conferred by the present solution is the densification of the magnetic field lines at the periphery of the shaft, which makes it possible to increase at the same time the applied torque and thus the driving power.

According to a preferred variant, the hollow central tubular part of the rotor is a cannulated shaft, the inner wall of which is adapted to form a suction channel for a microdebrider.

It is thus possible to improve the performance of such a motor compared with a conventional solution using radially oriented magnets while at the same time optimizing the given diameter of the inner duct of a cannulated shaft according to the desired flow properties.

According to an even more preferred embodiment, the inner wall of the cannulated shaft is made of austenitic stainless steel material.

One advantage of this solution is to facilitate the cleaning and sterilization process without the need for additional or dedicated ducts.

According to an even more preferred embodiment, the inner wall of the cannulated shaft is made of a material and/or covered with a coating that is hydrophobic and/or antimicrobial.

An advantage of this solution is that it facilitates fluid flow and/or counteracts blood and/or protein deposition and/or has an antimicrobial action. The inner wall of the cannulated shaft can therefore, for example, be coated with a fluoride-based polymer or a thin layer based on titanium oxide ($TiO2$) or other chemical compounds of titanium.

In a preferred embodiment, the said inner wall of the cannulated shaft is coated with alternating hydrophobic and hydrophilic layers.

The alternating arrangement of hydrophobic or superhydrophobic regions and hydrophilic or superhydrophilic regions further improves the efficiency of cleaning procedures.

According to still another preferred embodiment, the micromotor also comprises a coupling device to the abrasive blade which is arranged along the axis of rotation of the rotor.

Such a direct drive arrangement eliminates the need for any intermediate gear mechanism between the motor and the blade, which minimizes, on the one hand, the space required in the handpiece and, on the other hand, the power losses, thanks to a direct transmission.

According to a preferred embodiment, the rotor is formed by a single multipolar ring. Such a one-piece construction is advantageous for the rotor because it does not require combining previously magnetized blocks of material, thus avoiding a segment-by-segment assembly.

According to a variant, the rotor is formed by a plurality of multipolar rings, that is to say at least two.

According to this variant, the rotor is formed by two or more multipolar rings that can be mounted axially one on the other, either simply glued together or driven on the same cannulated shaft. This has little effect on the assembly process, which is carried out in segments; however, such a method of assembling several magnets axially makes it possible to create longer motors because there is a manufacturing constraint on the size ratios of the magnets. This solution also makes it possible to reduce the induced current in the rotor, which goes in the direction of a reduction of the losses (same concept as the lamination of the ferromagnetic parts).

According to another preferred embodiment, the rotor is formed by a magnetized plate of non-uniform thickness.

An advantage of such an arrangement for the rotor is that it makes it possible to optimize the distribution of the magnetic field.

According to a preferred variant, the stator is of slotted type.

In this type of motor construction, the volume of the stator is larger due to the presence of the teeth, and therefore the volume of the rotor is more limited and therefore the advantage conferred by the arrangement of a Halbach array is even more relevant in order to maximize the section of the hollow tubular part of the rotor potentially used as an internal suction channel while preserving the efficiency of the motor.

The present invention otherwise relates to a rotor for a rotary motor taken separately from the stator, characterized in that it comprises an outwardly polarized Halbach array, which element can be produced and sold separately from the rest of the motor.

BRIEF DESCRIPTION OF THE DRAWINGS

Other advantageous features will emerge more clearly from the description which follows of a particular embodiment of the invention given by way of non-limiting example and represented by the attached drawings in which:

FIGS. 2A and 2B are schematic views respectively illustrating a solution using a Halbach array, as in the scope of the present invention and a solution using a radial arrangement of magnets, without shielding;

DETAILED DESCRIPTION

In the following a preferred embodiment will be referred to for the micromotor according to the present invention, wherein it is integrated in a microdebrider 1.

Figure 1:
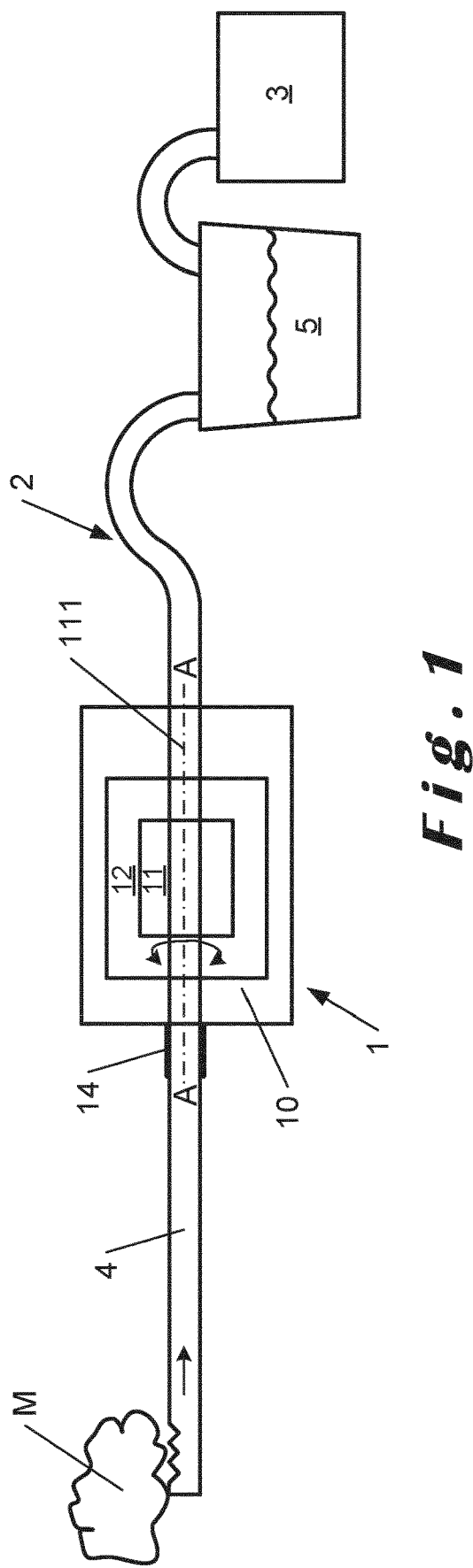
FIG. 1 is a schematic view of a tool using a cannulated shaft as in the scope of the present invention.

FIG. 1 is a schematic view of such a surgical tool, often referred to as a "shaver", aiming to eliminate or respectively remove material M such as soft tissue, via a rotating milling/grinding tool such as an abrasive blade 4, which is here directly coupled to a rotary motor 10 via a coupling device 14 such as, for example, a coupling nose (male element) inserted into a hole of the blade (female element). The motor 10 is conventionally composed of a stator 12 arranged concentrically around a rotor 11, the hollow central tubular part of which is formed by a cannulated shaft 111, the internal wall 111A of which constitutes a rectilinear conduit corresponding to the suction channel 2 of the microdebrider.

Preferably, this duct is made of a material or a coating layer intended to facilitate the flow of a fluid suctioned by a pump 3 located behind a filter unit 5 where the waste material is discharged in the direction of the arrow shown on the abrasive blade 4, and which corresponds to the path of the fluid and the waste material M suctioned inside the blade 4, which thus also has a hollow shape itself. For this purpose, layers or a surface treatment making the inner wall 111A hydrophobic can be used; according to a preferential embodiment, hydrophilic and hydrophobic regions can even be alternated in order to separate the deposition of blood and/or proteins removed or respectively torn off during the debriding operation, which will facilitate the cleaning operations.

According to a preferred embodiment, the suction channel 2 is made of austenitic stainless steel, for example type 316 L or 1.4301, in order to allow sterilization operations while avoiding any corrosion. The inner wall 111A of the cannulated shaft 111 forming the suction channel 2 may preferably be coated with a fluoride-based polymer or a thin layer of titanium oxide (TiO2) or other chemical compounds of titanium in order to have an antimicrobial action.

The advantage of the microdebrider 1 as shown in FIG. 1 is that no gear mechanism is required to transmit the rotation of the motor to the rotating milling tool, i.e. the grinding blade 4, which is directly coupled to the motor via the coupling device 14 arranged along the axis of rotation (A-A) of the motor. Thus, unlike microdebriders using a dedicated suction channel 2 separate from the rotary motor 10 which rotates around an axis offset from the abrasive blade 4, the space requirement is reduced and the transmission quality is increased since there is no longer any intermediate gear mechanism between the rotary motor 10 and the abrasive blade 4.

Furthermore, as explained in the following, the rotary motor 10 using an outwardly oriented Halbach array according to the invention allows for maximum efficiency while at the same time increasing the effective diameter of the suction channel 2, which were previously two parameters that could not be optimized simultaneously. FIGS. 2A and 2B provide a comparative explanation of how a Halbach array works compared with a conventional magnetization solution.

According to the principle of magnetic configuration of a Halbach array, the magnetized system does not consist of two or more pairs of poles, but of a combination of magnetized 'blocks' or 'zones' with inclinations adapted to cause the natural closing of the field lines without the need for soft ferromagnetic materials (soft steel, mu-metal). As illustrated in FIG. 2A, the Halbach array 61 uses a series of polarized magnets intended to eliminate the field lines inside the cylinder and to multiply by two the field strength (arrows corresponding to the magnetic field B doubled) compared to a conventional magnetization scheme with a radially polarized magnet 6, as illustrated in FIG. 2B, where the field lines are closed inside the cylinder and this precisely requires the use of a magnetic shielding via a suitable material such as the soft ferromagnetic materials mentioned above when one wishes to prevent any penetration of the field inside the cylinder, which is the case in particular when a fluid is flowing inside it as in the case of the microdebrider 1 illustrated in FIG. 1. In FIG. 2A, the directions of each of the magnetized parts shown are offset by 90 degrees from each other; however, in FIGS. 4A and 4B which follow, the directions of these arrows are offset by only 45 degrees, the idea being to represent the most continuous variation of the field orientation possible along the cylinder.

The outwardly polarized Halbach array 61 consists of bipolar permanent magnets or multipolar permanent magnets. The rotor according to the invention may therefore be made, for example, according to one of the following embodiments:

A) A rotor made up exclusively of one or more permanent magnets
B) A rotor consisting of a cannulated shaft made of diamagnetic, paramagnetic or 'weakly' ferromagnetic materials (magnetic permeability typically less than 100) located in the center of the rotor and extending in the axial direction, and of one or more permanent magnets located outside the cannulated shaft. According to this mode of realization, the permanent magnets are glued or driven on the inner cannulated shaft.
C) A rotor consisting of one or more permanent magnets and a tube made of diamagnetic, paramagnetic or 'weakly' ferromagnetic materials (magnetic permeability typically less than 100) located outside the group of permanent magnets. According to this method, the permanent magnets are glued or driven into the outer tube.

The rotor according to the invention has a mass percentage of ferromagnetic, permanently non-magnetized material, preferably below 10%. The rotor according to the invention has a mass percentage of permanently magnetized ferromagnetic material, preferably above 70%.

According to an optimal configuration, the maximum magnetic induction field at a distance of 2 mm from the outer surface of the rotor according to the invention, taken independently of the presence of a stator (i.e., for example, for a rotor taken in isolation before assembly or on a spare part following a disassembly-reassembly operation) will preferably be greater than 0.1 T, and even more preferably between 0.2 and 0.3 T.

Figure 3B:
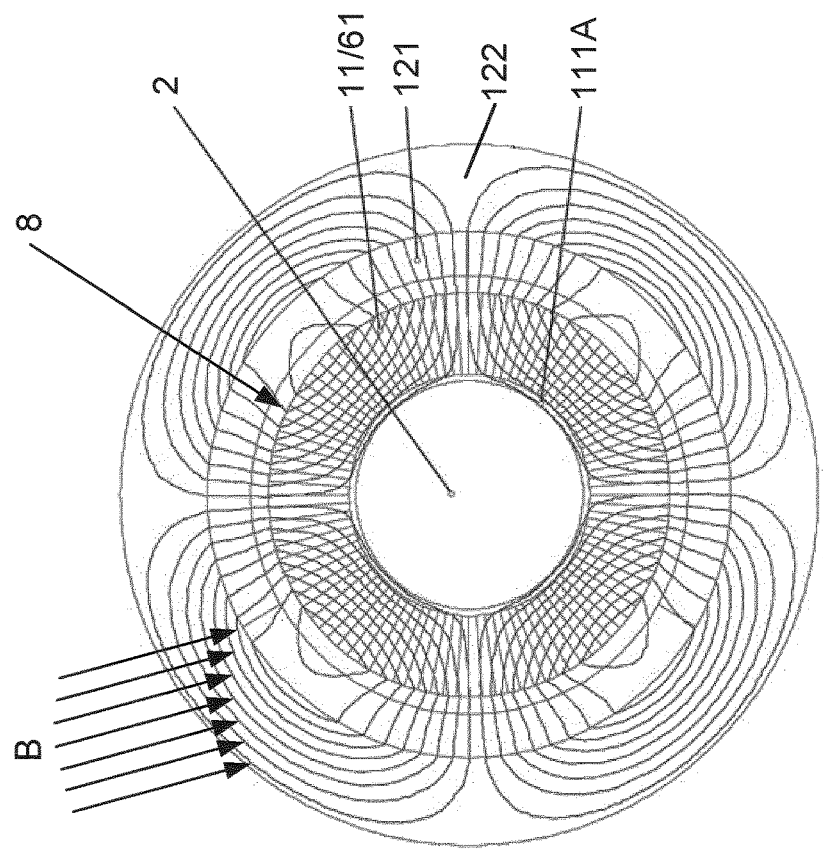
FIGS. 3A and 3B illustrate respectively cross-sectional views of a motor using respectively a radial arrangement of magnets as well as an internal shielding sheath, and in contrast a Halbach array for the rotor.
Figure 3A:
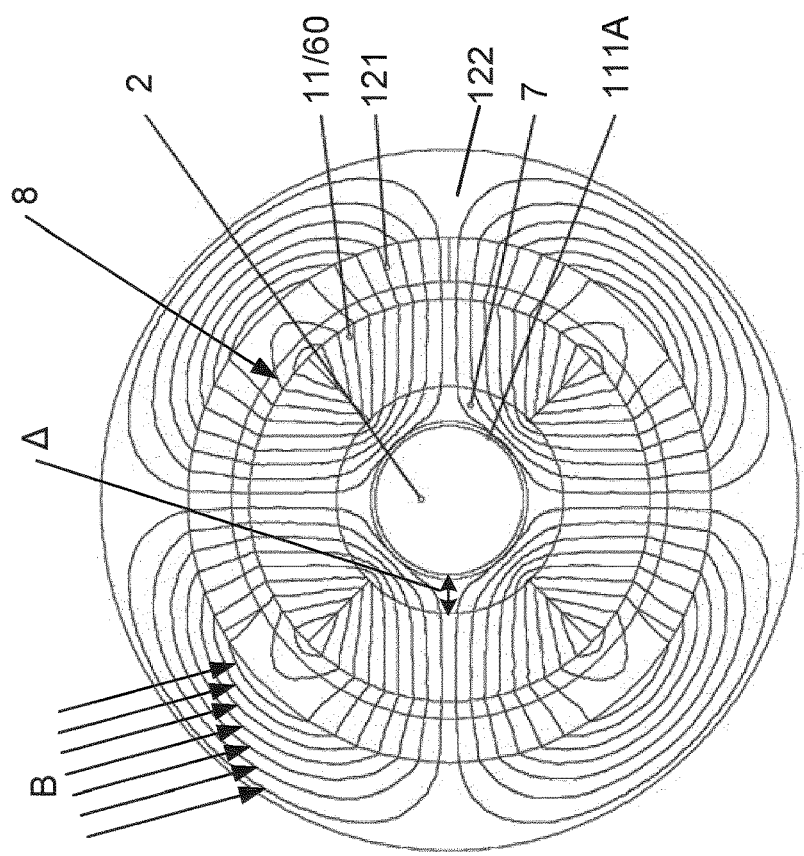

FIGS. 3A and 3B illustrate how, in the scope of the present invention, it is possible to both increase the diameter of the suction channel 2 and increase the torque of the rotary motor by confining the magnetic field to the periphery.

In FIG. 3A, the rotor 11 uses a radial arrangement of magnets 60 co-operating with the coils 121 of the stator 12, the lamination layers 122 of which can also be seen in one segment. The rotor 11 is separated from the rotor by a gap, commonly referred to as the air gap 8, and within it is formed a shielding layer 7 of ferromagnetic material. Comparing this FIG. 3A with FIG. 3B, it can be seen that all of the configuration elements of rotor 11 and stator 12 are identical, with the exception of shielding 7 constituting a ring of thickness A. This thickness differential makes it possible to increase the diameter of the suction channel 2 located inside the rotor 111 and the internal wall 111A of the cannulated shaft that it forms, without affecting the performance of the motor, since the field lines redirected towards the outside by the Halbach matrix 61 make it possible to densify the field lines at the periphery and consequently to increase the motor torque proportionally, and therefore the transmission efficiency.

According to a preferred embodiment, the internal diameter of the hollow central tubular part of the rotor according to the invention is preferably greater than 3 mm, and the motor torque is preferably between 10 and 100 mNm; according to a particularly preferred variant it is between 20 and 25 mNm. Thanks to such a configuration for the motor, it is now possible to jointly optimize these two parameters which were previously antagonistic and which therefore required a prioritization choice.

According to a preferred embodiment, the rotor 111 can be formed by a single multipolar ring and thus be realized in a completely monobloc configuration. However, according to an even more preferred embodiment, it can be realized by at least two multipolar rings driven on the cannulated shaft 111 and also be constituted by a plurality of magnetized plates of non-uniform thickness, in order to go in the direction of a reduction of the losses according to the same concept as the lamination of the ferromagnetic parts of the stator 121, such as those corresponding to the elements 122 illustrated in FIGS. 3A and 3B. However, in either case, it will be possible to form the multipolar ring on the basis of a magnetized plate of non-uniform thickness; in the case of a single ring, this can be achieved by a fluted shape, and in the case of a plurality of rings placed end-to-end in a segment-by-segment assembly, the thicknesses can vary between the different segments, so as to form a multi-stage cylinder, always with the same objective of varying the field as continuously as possible along the cylinder, and thus optimizing performance in terms of the torque resulting from the rotor drive.

Figure 4B:
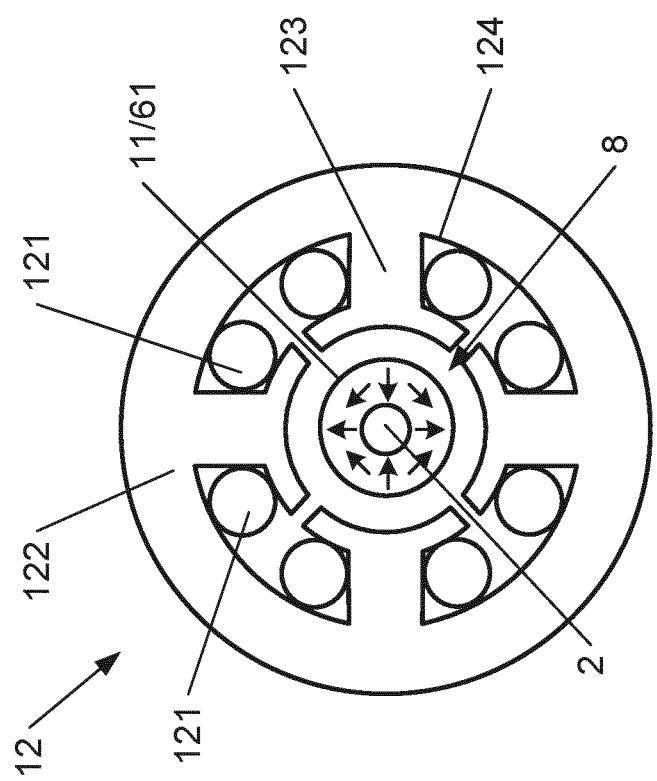
FIGS. 4A and 4B illustrate respectively variants with and without slot (slotted and slotless) that can be used in the scope of the present invention.
Figure 4A:
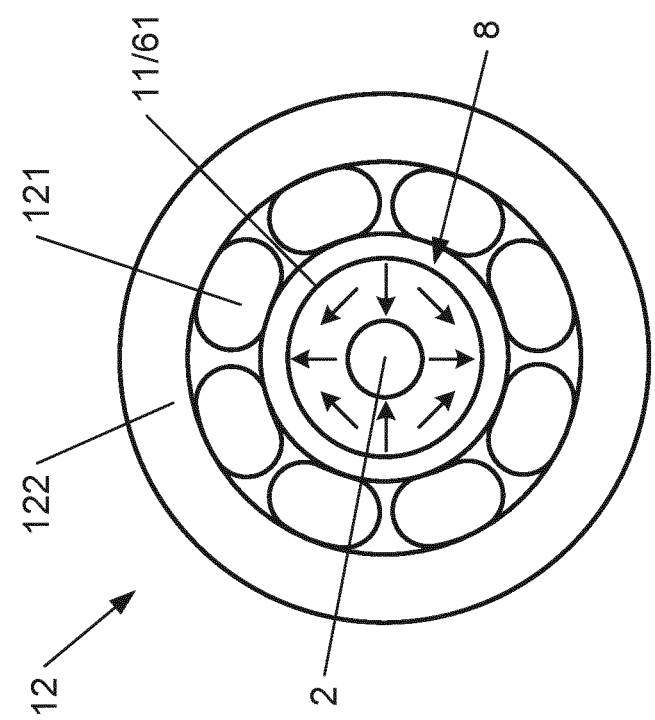

FIGS. 4A and 4B illustrate two stator variants which can be used in the context of the present invention, i.e. which can co-operate with a rotor 11 in which a Halbach matrix 61 is arranged. As in the previous FIGS. 3A and 3B, the stator 12 comprises lamination layers 122 and coils 121 co-operating with the rotor 11, preferably constituting a cannulated shaft in the center of which is arranged a suction channel 2. For the sake of readability, not all elements of the rotor 11 have been referenced in FIGS. 4A and 4B, which are only intended to describe two different types of stator 12, namely with or without slots ("slotted" or "slotless"). The rotor 11 is spaced from the stator 12 by an air gap 8 towards the inside of it.

In FIG. 4A corresponding to the "no slot" model, the stator yoke consists of a ring-shaped sheath, while in FIG. 4B corresponding to the "slot" model, different series of coils are arranged in slots 124 located between stator teeth 123. For the same values of windings, the slotted design is larger radially, and therefore the use of a Halbach array for the rotor to recover this internal space trimmed by the stator 12 is all the more appropriate—this is why the size of rotor 11 in FIG. 4A has been deliberately shown as being substantially larger than that in FIG. 4B.

Although the above-described embodiment is given as a non-limiting example, it is understood that it is not intended to be an exhaustive description of all possible embodiments.

One skilled in the art will understand that it is conceivable to replace a described means with an equivalent means without departing from the scope of the present invention.

LIST OF REFERENCE NUMERALS OR SYMBOLS

| | |
|---|---|
| 1 | microdebrider (shaver) |
| 10 | motor |
| 11 | rotor |
| 111 | cannulated shaft |
| 111A | inner wall |
| 12 | stator |
| 121 | coils of the stator |
| 122 | lamination layers of the stator |
| 123 | tooth of the stator |
| 124 | slot of the stator |
| 14 | coupling device |
| 2 | suction channel |
| 3 | pump |
| 4 | blade |
| 5 | filter unit |
| 6 | magnet |
| 60 | radial arrangement of magnets |
| 61 | outwardly polarized Halbach array |
| 7 | inner shielding |
| 8 | spacing/air gap |
| A-A | axis of rotation of the motor |
| M | material to be eliminated/debrided |
| B | magnetic field lines |
| Δ | thickness differential |

The invention claimed is:

1. Rotary micromotor designed for actuating an abrasive blade of a surgical or dental tool, said motor comprising a rotor co-operating with a stator, wherein the rotor has a hollow central tubular portion, and comprises an outwardly polarized Halbach array, said hollow central tubular portion of said rotor being a cannulated shaft, an inner wall of said cannulated shaft being adapted to form a suction channel for a microdebrider.

2. The rotary micromotor according to claim 1, wherein said inner wall of the said cannulated shaft is made of an austenitic stainless steel material.

3. The rotary micromotor according to claim 1, wherein said inner wall of the said cannulated shaft is made of a material and/or covered with a coating that is hydrophobic.

4. The rotary micromotor according to claim 1, wherein said inner wall of the said cannulated shaft is made of a material and/or covered with a coating that is antimicrobial.

5. The rotary micromotor according to claim 1, wherein said inner wall of the said cannulated shaft is covered with alternating hydrophobic and hydrophilic layers.

6. The rotary micromotor according to claim 1, further comprising a coupling device for coupling to the said abrasive blade arranged along an axis of rotation of said rotor.

7. The rotary micromotor according to claim 1, wherein said rotor is formed by a single multipolar ring.

8. The rotary micromotor according to claim 1, wherein said rotor is formed by at least two multipolar rings, driven on said cannulated shaft.

9. The rotary micromotor according to claim 1, wherein said rotor is formed by at least one magnetized ring of non-uniform thickness having a grooved shape, or a plurality of rings placed end to end segment by segment and whose respective thicknesses differ according to the segments.

10. The rotary micromotor according to claim 1, wherein said stator is of the slotted type.

11. Microdebrider comprising the rotary micromotor according to claim 1.

* * * * *